United States Patent
Vinci et al.

(10) Patent No.: US 8,679,326 B2
(45) Date of Patent: Mar. 25, 2014

(54) MEDICAL APPARATUS FOR EXTRACORPOREAL TREATMENT

(75) Inventors: Luca Vinci, Poggio Rusco (IT); Andrea Rossi, San Giacomo delle Segnate (IT)

(73) Assignee: Gambro Lundia AB, Lund (SE)

( * ) Notice: Subject to any disclaimer, the term of this patent is extended or adjusted under 35 U.S.C. 154(b) by 383 days.

(21) Appl. No.: 12/809,031

(22) PCT Filed: Dec. 16, 2008

(86) PCT No.: PCT/IB2008/003504
§ 371 (c)(1),
(2), (4) Date: Jun. 17, 2010

(87) PCT Pub. No.: WO2009/090473
PCT Pub. Date: Jul. 23, 2009

(65) Prior Publication Data
US 2010/0300945 A1   Dec. 2, 2010

(30) Foreign Application Priority Data
Dec. 20, 2007   (IT) .............................. MI2007A2397

(51) Int. Cl.
  *B01D 35/00*   (2006.01)
  *G08B 21/00*   (2006.01)
  *A61M 31/00*   (2006.01)
(52) U.S. Cl.
  USPC ............ 210/85; 210/745; 210/104; 340/605; 340/618; 340/619; 604/65; 604/67
(58) Field of Classification Search
  None
  See application file for complete search history.

(56) References Cited

U.S. PATENT DOCUMENTS

| | | | |
|---|---|---|---|
| 3,661,119 A * | 5/1972 | Sanders | 119/217 |
| 5,591,344 A | 1/1997 | Kenley et al. | |
| 5,630,935 A | 5/1997 | Treu | |
| 5,645,734 A | 7/1997 | Kenley et al. | |
| 5,651,893 A | 7/1997 | Kenley et al. | |
| 5,658,456 A | 8/1997 | Kenley et al. | |
| 5,670,050 A | 9/1997 | Brose et al. | |
| 5,674,390 A * | 10/1997 | Matthews et al. | 210/261 |
| 5,674,397 A | 10/1997 | Pawlak et al. | |
| 5,674,404 A | 10/1997 | Kenley et al. | |
| 5,690,821 A | 11/1997 | Kenley et al. | |
| 5,690,831 A | 11/1997 | Kenley et al. | |
| 5,697,248 A | 12/1997 | Brown | |
| 5,702,606 A | 12/1997 | Peter, Jr. et al. | |
| 5,705,066 A | 1/1998 | Treu et al. | |
| 5,707,086 A | 1/1998 | Treu et al. | |
| 5,714,060 A | 2/1998 | Kenley et al. | |
| 5,725,776 A | 3/1998 | Kenley et al. | |

(Continued)

FOREIGN PATENT DOCUMENTS

| | | | | |
|---|---|---|---|---|
| DE | 29 27 449 A1 | 1/1981 | | |
| DE | 2927449 A1 * | 1/1981 | .......... | G01F 23/2928 |

(Continued)

*Primary Examiner* — Nam Nguyen
*Assistant Examiner* — Richard Gurtowski
(74) *Attorney, Agent, or Firm* — Pearne & Gordon LLP

(57) ABSTRACT

A medical apparatus (100) for extracorporeal blood treatment comprises a support structure (101) housing a hydraulic circuit (1) located above a liquid collection zone (103) such that liquid losses from the hydraulic circuit can at least partially accumulate at the liquid collection zone. A liquid sensor (108) detects presence of any liquid in the liquid collection zone and operates in a distanced position with respect to the liquid collection zone (103).

26 Claims, 9 Drawing Sheets

(56) References Cited

U.S. PATENT DOCUMENTS

| | | | |
|---|---|---|---|
| 5,788,099 A | 8/1998 | Treu et al. | |
| 5,932,110 A | 8/1999 | Shah et al. | |
| 5,938,304 A * | 8/1999 | Irby et al. | 312/229 |
| 6,581,461 B1 * | 6/2003 | Diaz | 340/619 |
| 2005/0010157 A1 * | 1/2005 | Baraldi et al. | 604/4.01 |

FOREIGN PATENT DOCUMENTS

| | | |
|---|---|---|
| DE | 195 16 789 A1 | 11/1996 |
| GB | 2 199 436 A | 7/1988 |
| GB | 2 272 553 A | 5/1994 |
| WO | 2004/096322 A1 | 11/2004 |

\* cited by examiner

FIG 8
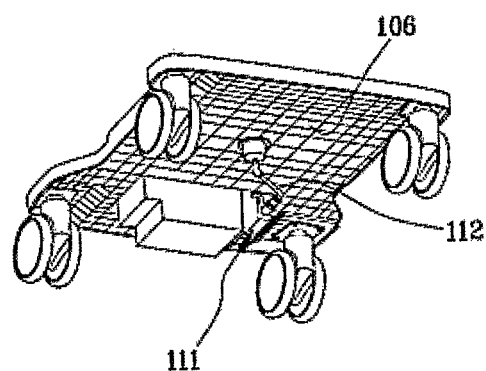
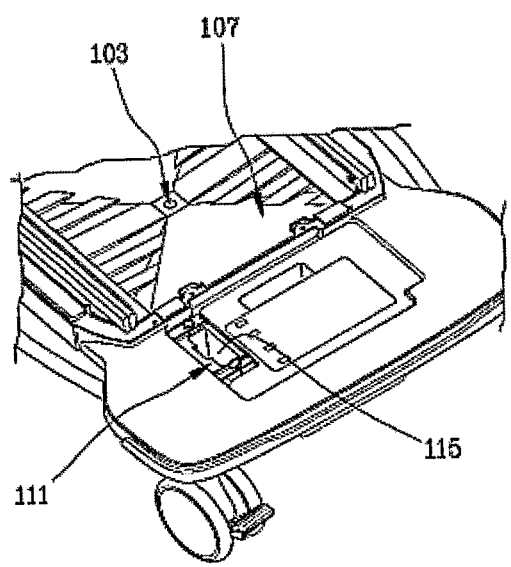
FIG 7

MEDICAL APPARATUS FOR EXTRACORPOREAL TREATMENT

As is known, machines for blood treatment, such as for example machines for kidney failure or hepatic insufficiency treatments, or machines for plasmapheresis or machines for other treatments, can comprise a hydraulic circuit which has the task of removing one or more liquids from a source, taking those liquids towards a treatment zone and removing the used liquid or liquids downstream of the treatment zone in order to evacuate them towards a discharge zone.

By way of example, in machines for treatment of chronic kidney failure, one or more liquid sources contribute to form a fresh treatment liquid which is taken from a channel towards a treatment zone. In particular, the treatment zone comprises one or more semipermeable membrane treatment units where the treatment liquid exchanges solid and liquid substances with the blood subjected to treatment. The most typical therapies are hemodialysis, hemofiltration, hemodiafiltration, ultrafiltration and plasmapheresis. Machines for kidney failure treatment can carry out one or more of the above-listed treatments.

Downstream of the treatment unit or units, a discharge channel takes the used treatment liquid towards one or more discharges.

The hydraulic circuit briefly described above comprises numerous components, such as: pumps, valves, tubes, sensors etc., which are connected to one another. It is thus obvious that during use of the machine, an undesirable liquid leak from the hydraulic circuit might occur at one or more of the junctions between the various components, or due to breakage of one or more components. In the dialysis sector, due to the continuous treatment cycles, the variability of the pressures, the disinfection cycles, seal problems can emerge over time, due to wear.

Although the hydraulic circuits are clearly designed to guarantee optimal functioning in all operating conditions, it is obvious that possible liquid leakage can occur over the lifespan of a machine for blood treatment. It is also clear that possible liquid leaks, apart from causing undesirable losses of material, can damage the dialysis machine and can be dangerous for the patient undergoing treatment. If for example excessive liquid leakage impinges on components sensitive to contact with liquid, the components might be irreparably damaged, compromising the operativity of the whole machine. If these leaks were to go unnoticed, they might compromise control of the fluid balance in the patient, with possible consequences for the well-being of the patient him or herself.

A known technical solution in the sector of dialysis is described in U.S. Pat. No. 5,674,390, in which a dialysis machine exhibits a shaped bottom housing, at the lowest point thereof, a liquid leakage sensor.

A second known solution is illustrated in document WO2004096322 which concerns a device for detecting leakage in dialysis machines constituted by a container which collects leakage and two liquid level sensors.

Finally, documents GB2199436 and GB2272553 describe devices for detecting fluid loss from apparatus located above them. The described devices comprise shaped bottoms with a zone of maximum depth where the leaked fluid collects, the zone being located in a central zone of the bottom, or a corner zone thereof.

An aim of the invention is to make available an easily-implemented medical apparatus for extracorporeal blood treatment which can reliably detect liquid leakage.

A further aim of the invention is to make available a medical apparatus for extracorporeal blood treatment in which maintenance and/or inspection of the liquid sensor or sensors used is easy.

A further aim of the invention is to make available a medical apparatus where the liquid sensor or sensors do not operate in direct contact with the liquid.

A further aim of the invention is to make available a medical apparatus which can switch to a security mode in a case of liquid leakage.

One or more of the specified aims is attained by a medical apparatus for extracorporeal blood treatment, comprising:
- a support structure internally exhibiting a housing chamber including at least one liquid collection zone;
- a hydraulic circuit having at least one supply channel, destined to transport a treatment liquid from at least one source towards a treatment station, and at least one discharge channel, destined to transport a used liquid from the treatment station towards an evacuation zone, the hydraulic circuit being located in the housing chamber above the liquid collection zone such that the leakage of liquid from the hydraulic circuit can in part accumulate at the liquid collection zone,
- a liquid sensor destined at least to detect any liquid in the liquid collection zone, characterised in that the liquid sensor operates in a distanced position with respect to the liquid collection zone.

The support structure exhibits at least one lateral wall substantially delimiting the housing chamber and a bottom arranged in a lower portion of the support structure and comprising at least the liquid collection zone; the liquid sensor is located in a position which is distanced from the bottom.

Since the sensor is distanced from the bottom, the inspectability thereof is facilitated, as is the maintenance. Further, the fact of being distanced from the collection zone means that insignificant liquid leakage can be ignored.

In the present embodiment, the liquid sensor is located in a vertically-distanced position from the bottom. More precisely, the sensor is located in a distanced position which is vertically raised with respect to the liquid collection zone. For example, the sensor can be raised by 20-40 cm with respect to the bottom, or can operate in a measuring chamber located laterally with respect to the housing chamber.

The bottom can exhibit a non-horizontal shape: in this case the liquid collection zone (in reality numerous liquid collection zones might be included, distanced from one another and distributed around the bottom) is located in a zone of maximum depth of the bottom, so that the force of gravity forces any leaks coming from the hydraulic circuit to collect there. The collection zone or zones, then, are located on the bottom and receive and collect the liquid due to the position and geometry of the bottom.

From a structural point of view, the bottom can comprise a wall which extends transversally of the lateral wall substantially at a base zone of the support structure. The liquid sensor is located in a distanced position with respect to the upper surface of the wall, i.e. it is not in contact with the surface, but operates either externally of the housing chamber or, if located internally thereof, it operates in a position which is detached from the bottom wall which collects and conveys the liquid towards the collection chamber.

Depending on the particular embodiment, the bottom wall extends over the whole transversal section of the container body and exhibits a perimeter edge which is sealingly joined to the lateral wall thereof such that any substance which falls from the components contained in the container body can be collected on the bottom wall. Alternatively the bottom wall can extend such as to exhibit a perimeter edge which develops in proximity of and adjacent to an internal surface of the lateral wall.

In an embodiment of the invention, at least one measuring chamber is afforded externally of the housing chamber and a channel which sets the liquid collection zone or zones in communication with the measuring chamber. If more than one collection zone is included on the bottom, several channels could be included, leading to a single measuring chamber or leading to separate measuring chambers. Each channel exhibits a first end, directly connected to a lower point of the respective collection zone, and a second end, directly connected to a lateral wall of the measuring chamber. As for the nature of the liquid sensor operating in the measuring chamber or chambers, it can be either a liquid-presence sensor operating in the measuring chamber, i.e. a sensor that is sensitive only to the presence of liquid. This sensor is located at a height which is vertically above the lowest point of the collection zone and emits a measuring signal when the liquid level in the measuring chamber is greater than or equal to a predetermined level, for example when the level exceeds the level in which the liquid-presence sensor itself is operating. Alternatively a liquid level sensor can be used, operating at the measuring chamber and emitting a measuring signal which is proportional to the liquid level in the measuring chamber. In another aspect of the first embodiment, the collection chamber can comprise an upper inspection opening developing substantially horizontally and externally of the lateral wall of the support structure in order to enable direct access to the measuring chamber and therefore to the sensor.

In a further embodiment the at least one liquid sensor can comprise a member emitting a signal and a member receiving the signal, the receiving member operating in the housing chamber above and at a predetermined distance from the bottom. In this case it is not necessary that the liquid sensor enter into contact with the liquid. For example, the emitting member can operate internally of the housing chamber above and at a predetermined distance from the bottom such as to emit a signal crossing the collection zone (and thus any liquid accumulated in the collection zone) to be then reflected by the upper surface of the bottom towards the receiver member. The receiver member, according to the reflected signal received, can generate a measuring signal linked to the quantity of liquid present in the collection zone. It is specified that in an embodiment the emitter member can work at the bottom, for example at the collection zone. Further, the receiving member can be constituted by a single sensor member or by a plurality of members adequately distributed on the transversal section of the housing chamber. As for type, the emitting member can comprise a member selected from a group comprising: an emitter of an optic signal, an acoustic signal, an electric or electromagnetic signal. Similarly, the receiver can comprise a member selected from a group comprising: a receiver of an optic signal, an acoustic signal, an electric or electromagnetic signal.

In combination with one or more of the above-described characteristics, the medical apparatus can also comprise a user interface and a programmed control unit connected to the liquid sensor and the user interface. The control unit can for example comprise one or more digital microprocessor units or one or more analog type units, or combinations of analog units and digital units. In reference by way of example to a microprocessor unit, once the unit has performed a program (for example a program coming from the outside or directly integrated into the microprocessor card) the unit itself becomes programmed, so that a plurality of functional blocks are defined, which constitute means each designed to perform respective operations. In an aspect of the invention, the programmed control unit defines means as specified herein below:

means for receiving a measuring signal from the liquid sensor corresponding to a detection of the presence of liquid and/or liquid level; and means for determining, depending on the measuring signal, occurrence or not of an alarm condition.

In a further aspect of the invention, the programmed control unit can define means for commanding the user interface to generate a corresponding acoustic and/or visible signal, should the existence of an alarm condition be detected.

In combination with one or more of the above-described characteristics, the medical apparatus can comprise at least one safety device operating in correspondence with at least the supply channel and commandable between at least one first operating condition, in which the safety device enables a liquid flow along the supply channel towards the treatment zone, and a second operating condition, in which the safety device prevents passage of liquid towards the treatment zone. In this case, the control unit can be connected to the safety device and programmed to define means for commanding the safety device to pass from the first to the second operating conditions, should an alarm condition be detected. In an embodiment, the safety device can for example comprise at least one intercept member connected to the control unit; the intercept member in the first operating condition and on command of the control unit closing the fluid passage from said source along the supply channel.

The safety device can also comprise a bypass line connecting the supply channel and the discharge channel, and one or more fluid check members connected to the control unit with the aim of selectively opening and closing the bypass channel and the supply channel downstream of the bypass channel. On command of the control unit the check members of the first operating condition close the fluid passage towards the treatment zone and connect the source with the discharge channel through the bypass line.

Since the medical apparatus for blood treatment can comprise various liquid sources (for example one or more water sources, one or more concentrate sources, one or more liquid disinfectant sources) connected to the supply channel with respective delivery lines, the medical apparatus can exhibit, at each delivery line, a respective check member (for example comprising a valve member or an occlusive pump).

In combination with one or more of the above-described characteristics, the medical apparatus can comprise electrical supply means (one or more power suppliers and the necessary electrical power components, in itself of known type) connectable to a source of electric power, external to the apparatus and destined to supply electrical energy to the medical apparatus itself. In a further variant, the programmed control unit can be programmed for controlling means for cutting off the electrical supply (such as a switch connected to the control unit) to the supply means on occurrence of said alarm condition.

In combination with one or more of the above-described characteristics, the support structure of the medical apparatus can comprise:

a predetermined number of internal walls which separate the housing chamber into the following sub-compartments:

an upper chamber extending at the upper end of the housing chamber and housing the electronic circuitry inclusive of the control unit, a first intermediate chamber located at a vertically intermediate zone of the housing chamber, inferiorly with respect to the upper chamber, the first intermediate chamber housing the electrical supply devices, a second intermediate chamber located at a vertically intermediate zone of the housing chamber, inferiorly with respect to the upper chamber and adjacent to the first intermediate chamber, the second intermediate chamber housing one or more motor members and one or more actuators, a lower chamber, extending inferiorly of the intermediate chambers and above said bottom and housing the hydraulic circuit, the liquid sensor also being housed in the lower chamber.

When the sensor is operating in the lower chamber, the programmed control unit can include:

means for receiving a measuring signal from the liquid sensor corresponding to a detection of the presence of liquid and/or the liquid level;

means for calculating, depending on the measuring signal, the occurrence or not of an alarm condition, in which the means for determining the alarm condition reveal the existence of an alarm condition before a liquid level in the bottom reaches the liquid sensor.

In other words the sensor is vertically distanced from the collection zone and the programmed control unit is such programmed that an alarm is set off before the liquid level reaches the sensor and therefore the sensor is protected from any possible immersion in the liquid.

Some preferred embodiments of the present invention will now be described with the aid of the accompanying figures of the drawings, provided purely by way of non-limiting example, and in which:

FIG. 1 schematically illustrates the hydraulic circuit and the blood circuit of a medical apparatus for extracorporeal blood treatment;

FIG. 2 schematically illustrates a section of a lower portion of a medical apparatus in an embodiment of the present invention;

FIG. 3 schematically illustrates a section of a lower portion of a medical apparatus in a further embodiment of the present invention;

FIG. 4 schematically illustrates in side elevation the support structure of an apparatus of the embodiments of FIGS. 3 and 4;

Figure 1:
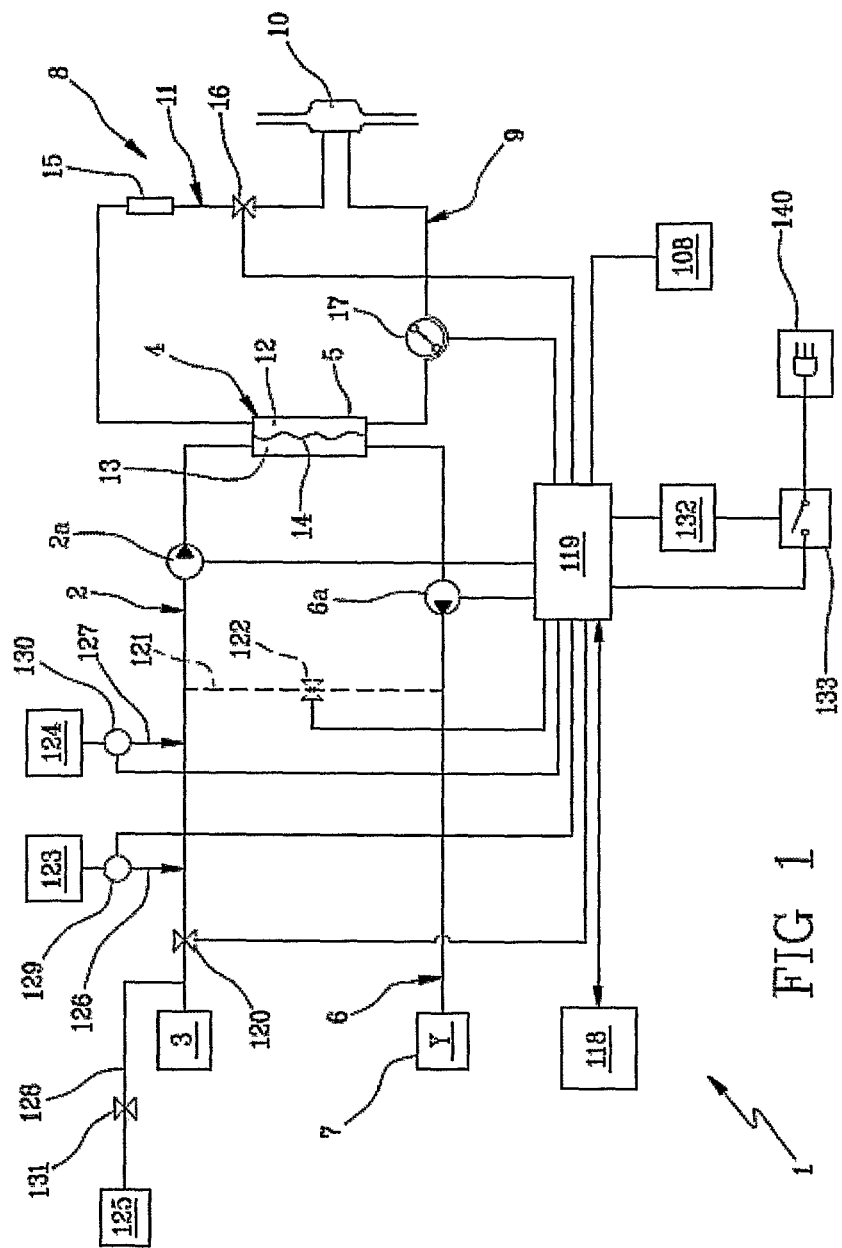
Figure 2:
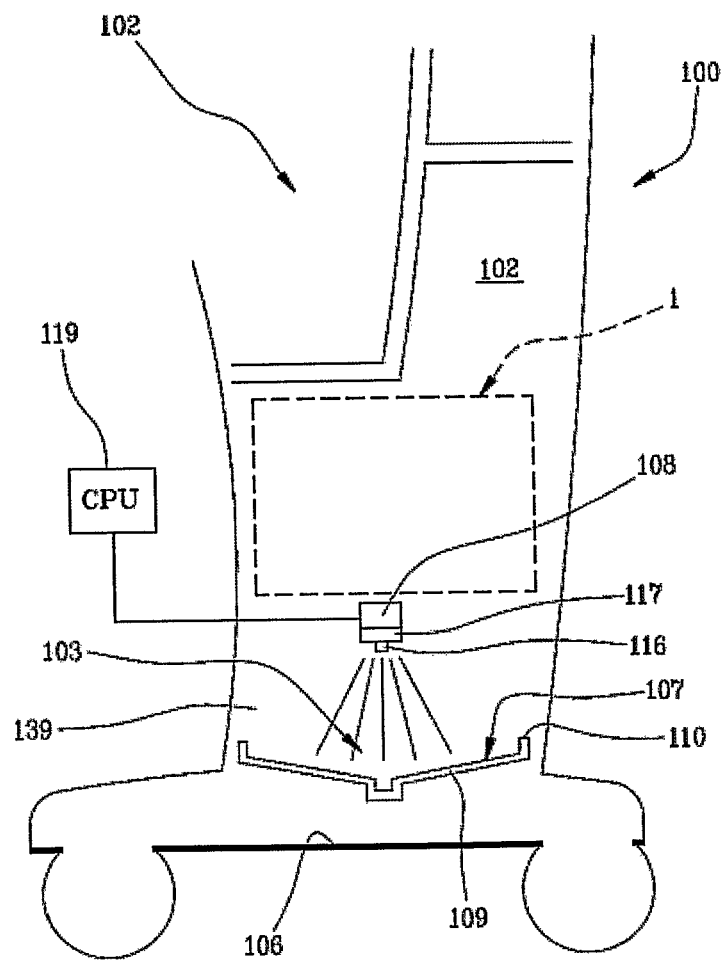

With reference to the accompanying figures of the drawings, 100 denotes a medical apparatus for extracorporeal blood treatment, in an embodiment of the invention.

The apparatus 100 comprises a support structure 101 internally exhibiting a housing chamber 102 which includes at least one liquid collection zone 103. The support structure exhibits at least one lateral wall 104 substantially delimiting the housing chamber 102. In the illustrated example, the lateral wall extends in a vertical direction, superiorly joining a terminal portion of head 105, while inferiorly exhibiting a terminal portion of base 106, which cooperate with the lateral wall 104 to define a box structure in which various components of the apparatus for dialysis are housed. Different support structures from those described can be included: for example the terminal base portion is absent in some machines and the lateral wall, in that case, defines a housing chamber that is inferiorly open.

The support structure further comprises a bottom 107 arranged at a lower portion of the support structure. In particular, the bottom is located above the terminal base portion 106, if this is present, as in the illustrated embodiment. The bottom 107 comprises the liquid collection zone or zones 103 should these be more than one in number.

The apparatus further comprises a hydraulic circuit 1. An embodiment of the hydraulic circuit is for example schematically illustrated in FIG. 1. Note that the specific structure of the hydraulic circuit 1 is not relevant for the purposes of the present invention and therefore other and different circuits to those specifically shown in FIG. 1 might be used in consequence of the functional and design needs of each single medical apparatus.

The hydraulic circuit 1 exhibits at least one supply channel 2, destined to transport a treatment liquid from at least one source 3 towards a treatment station 4 where one or more blood treatment units 5 operate. The circuit 1 further comprises at least one discharge channel 6, destined for the transport of a used liquid from the treatment station 4 towards an evacuation zone, schematically denoted by 7 in FIG. 1.

Figure 3:
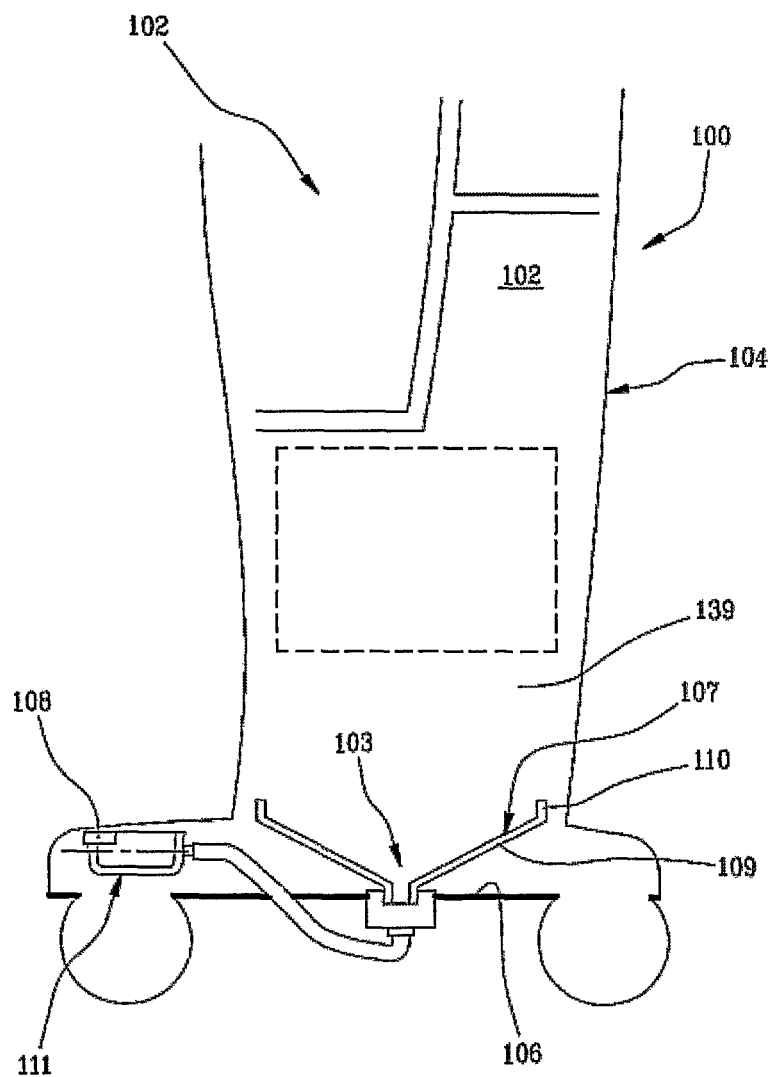
Figure 4:
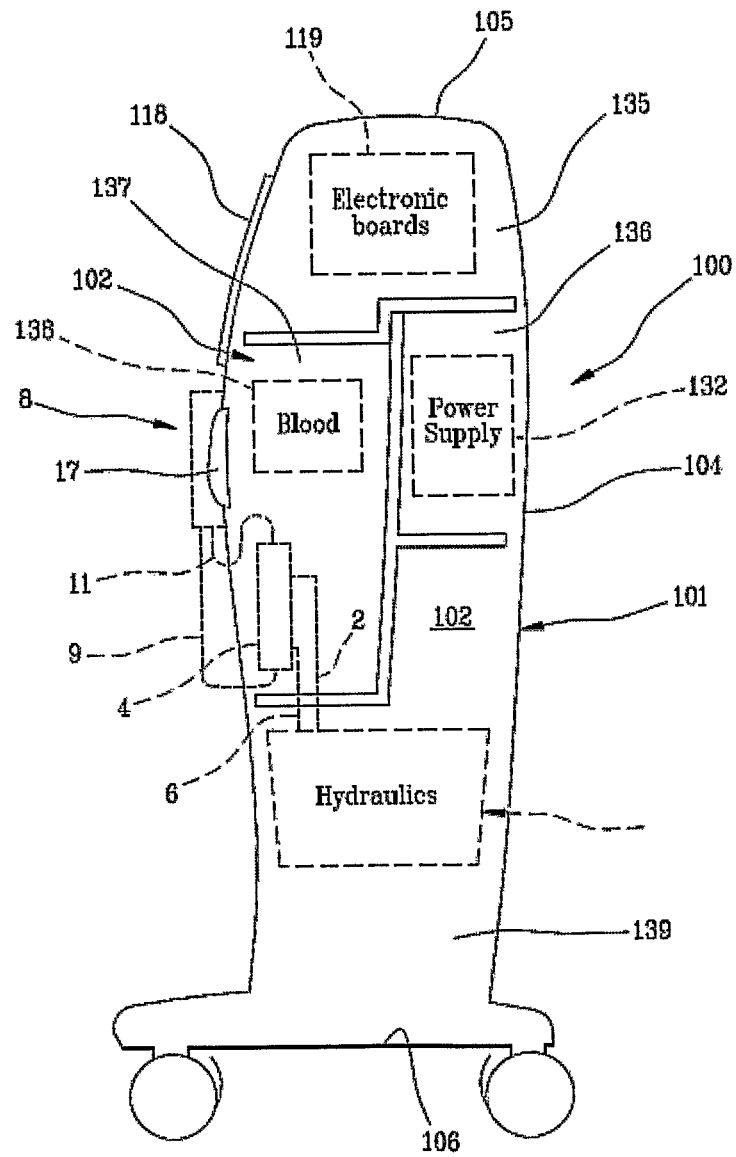
Figure 6:
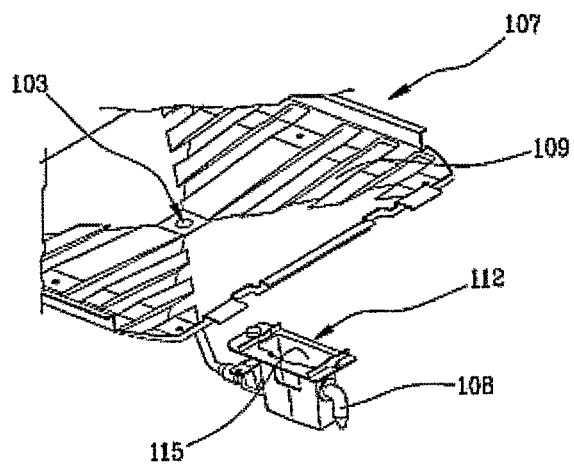
FIG. 6 is a perspective view of the bottom wall and the measuring chamber of the embodiment of FIGS. 3 and 5, and FIGS. 7 and 8 are perspective views from different angles of the contents of FIG. 5.
Figure 5:
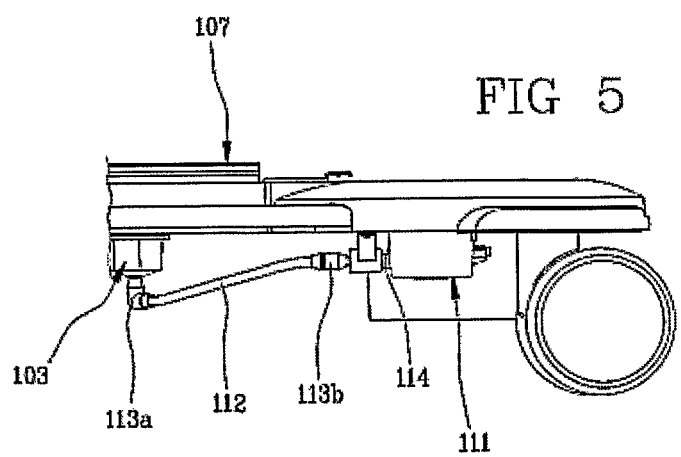
FIG. 5 is a side view of some details of the lower portion of the embodiment of FIG. 3.
Figure 9:
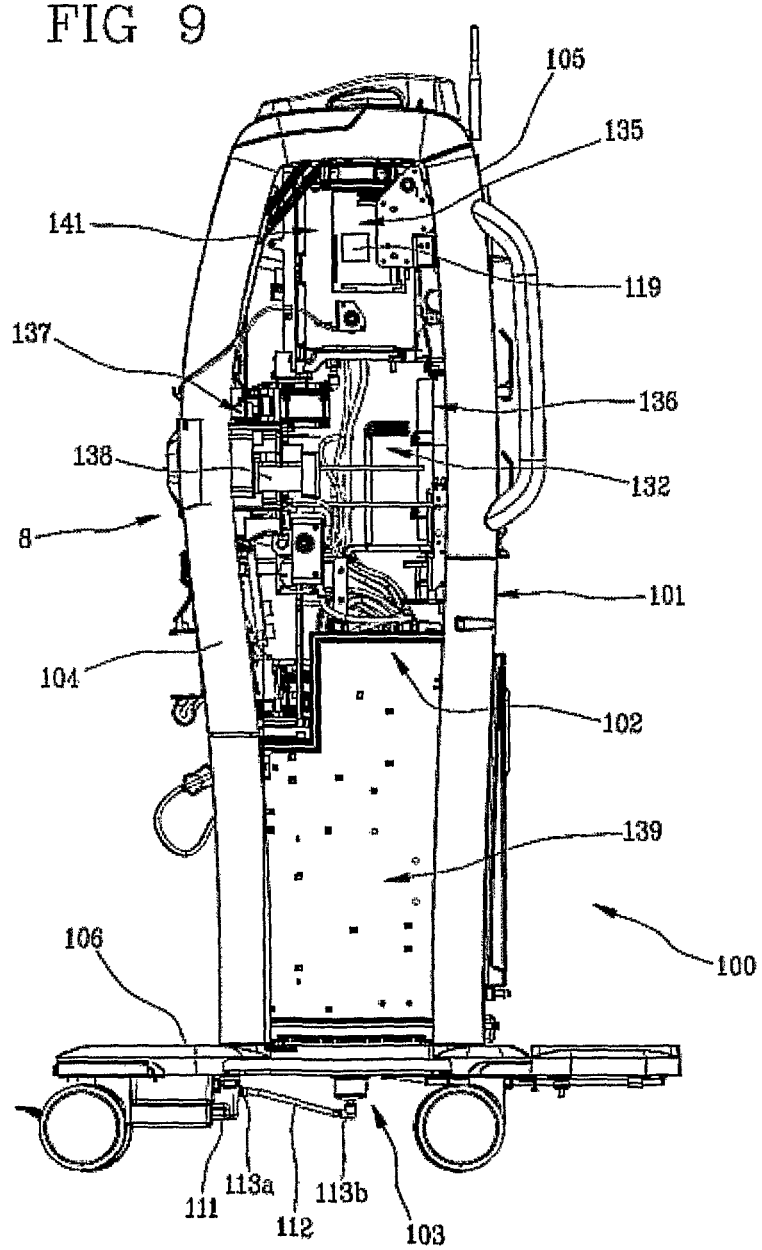
FIGS. 9 and 10 are elevations from opposite sides of the medical apparatus of the embodiment of FIG. 3, in which lateral closing panels have been removed to give a clearer picture of the internal components thereof.
Figure 10:
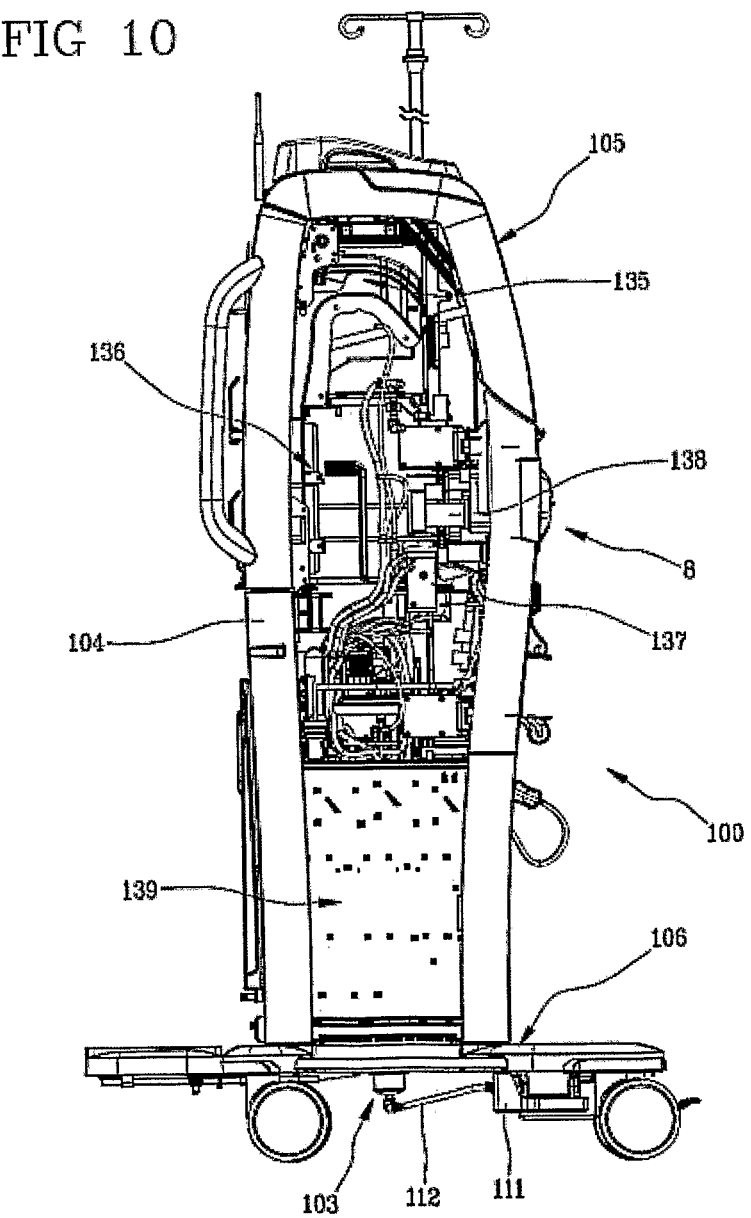
Figure 11:
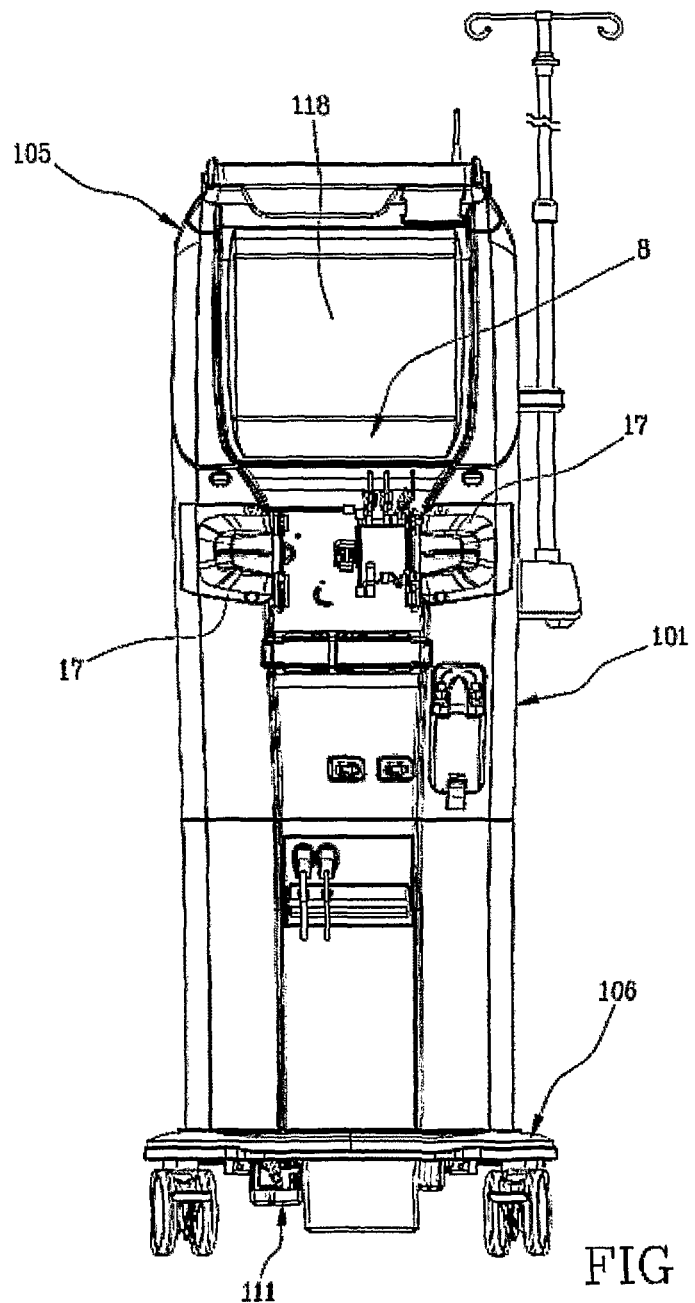
FIG. 11 is a front elevation of the apparatus of FIG. 9.

The hydraulic circuit 1 is located in the housing chamber above the liquid collection zone 103, such that liquid leakage from the hydraulic circuit can at least partially accumulate at the liquid collection zone itself; FIGS. 3 and 4 show that as for location, the hydraulic circuit 1 (schematically represented by a rectangular frame in a broken line) can be housed in the lower chamber 139, which, as will be more fully described herein below, constitutes one of the parts into which the housing chamber 102 is divided. The hydraulic circuit cooperates with a blood circuit 8, also schematically represented in FIG. 1 in its basis component parts. The specific structure of the blood circuit is also not fundamental, with reference to the present invention. Thus, with reference to FIG. 1, a brief description of a possible embodiment of a blood circuit is made, which is however provided purely by way of non-limiting example.

The blood circuit 8 of FIG. 1 comprises an arterial line 9 designed to remove blood from a vascular access 10 and a venous line 11 designed to return the treated blood to the vascular access. The blood circuit of FIG. 1 further comprises a first chamber, or blood chamber, 12 of the blood treatment unit 5, the second chamber 13 of which is connected to the hydraulic circuit 1. In greater detail the arterial line is connected at the inlet to the blood chamber 12, while the venous line is connected at the output to the blood chamber 12. In turn, the supply channel 2 is connected at the inlet to the second chamber 13, while the discharge channel is connected at the outlet to the second chamber. The blood treatment unit 4, for example a dialyzer or an ultrafilter or a plasma filter or a hemofilter or a hemodiafilter, comprises, as mentioned, the two chambers 12 and 13 which are separated by a semipermeable membrane 14, for example of the hollow-fibre type or plate type. The blood circuit can also comprise one or more separators 15: in the example of FIG. 1 a separator 15 is included at the venous line 11, upstream of a safety valve 16. The valve 16 can be activated to close the venous line when, for example, for security reasons the blood return to the vascular access 10 has to be halted. The apparatus 100 can also comprise one or more blood pumps 17, for example positive displacement pumps such as peristaltic pumps; in the example of FIG. 1, a pump 17 is included on the arterial line 9.

As mentioned, the hydraulic circuit 1 is housed internally of the chamber 102. In the illustrated embodiment the blood circuit 8 is instead borne on a front panel of the apparatus 100, which also supports the peristaltic pump or pumps 17. The treatment unit 5 can be physically supported by the lateral wall 104, and, in operating conditions of blood treatment, is connected both to the hydraulic circuit and to the blood circuit, as already illustrated (note that in FIG. 4 the blood circuit 8 and the unit 4 are represented with a broken line and schematically inasmuch as they are known).

A liquid sensor 108, destined at least to detect any liquid in the liquid collection zone 103, operates in a distanced position with respect to the collection zone itself. More precisely, when, as in the illustrated embodiment, the support structure comprises a bottom 107 arranged at a lower portion of the support structure and comprising the liquid collection zone 103, the liquid sensor is located at a distanced position and is thus not in contact with the bottom 107.

Since the sensor is distanced from the bottom, it is easier to inspect and maintain. Further, the fact of being distanced from the collection zone means that insignificant leakage of liquid can be ignored.

In an embodiment, should the sensor be operating internally of the housing chamber, it is located in a position which is distanced and vertically raised with respect to the liquid collection zone. For example, the sensor can be distanced by 20-40 cm from the bottom. Alternatively, the sensor can operate in a measuring chamber located laterally and externally with respect to the housing chamber.

In turn, the bottom 107 can exhibit a non-horizontal shape, as illustrated in the figures of the drawings in which the upper surface of the bottom converges in a downwards direction at an axially central zone of the bottom; in this case the liquid collection zone (in reality numerous collection zones could be provided in reciprocally distanced positions, and distributed throughout the bottom) is arranged in a zone of maximum depth of the bottom in order to receive, by free fall, any liquid leakage coming from the hydraulic circuit. In practice, the collection zone or zones are located on the bottom and receive and collect the liquid thanks to the position and geometry thereof.

From a structural point of view, the bottom can comprise a wall 109 extending transversally of the lateral wall substantially at a base zone of the support structure. The liquid sensor is located in a distanced position with respect to the upper surface of the wall, i.e. it is not in contact with the surface, but operates either externally of the housing chamber or internally of the housing chamber, in which case it operates in a detached position from the bottom wall, which collects and conveys the liquid towards the collection chamber.

Depending on the embodiments, the bottom wall extends over the whole transversal section of the container body and exhibits a perimeter edge 110 joined, for example sealingly, to the lateral wall 104, such that any substance falling from the components contained in the container body can be collected by the bottom wall.

Alternatively, the bottom wall can extend such as to exhibit a perimeter edge 110 developing in proximity of and adjacently to an internal surface of the lateral wall.

In a further embodiment of the invention (FIGS. 3, 5-8), at least one measuring chamber 11 is arranged externally of the housing chamber 102 and a channel 112 which sets the liquid collection zone or zones in communication with the measuring chamber. Should more than one liquid collection zone be afforded on the bottom, several channels could be included, leading to a single measuring chamber or separate measuring chambers. Each channel 112 exhibits a first end, directly connected to a lower point 113*a* of the respective collection zone, and a second end 113*b*, directly connected at a lateral wall 114 of the measuring chamber 111. As for the nature of the liquid sensor operating in the measuring chamber or chambers, it can comprise a liquid-presence sensor operating in the measuring chamber: i.e. a sensor which is only sensitive to the presence of liquid; the sensor being located at a height which is vertically above the lowest point of the collection zone and emits a measuring signal when the liquid level in the measuring chamber is greater than or equal to a predetermined level, for example when the level exceeds the level at which the presence sensor operates. An alternative choice for a liquid sensor is a liquid level sensor operating in the measuring chamber and able to emit a measuring signal proportional to the liquid level present in the measuring chamber. In a further aspect of the first embodiment, the collection chamber can comprise an upper inspection opening 115 developing substantially horizontally and externally of the lateral wall 104 of the support structure in order to enable direct access to the measuring chamber and thus the sensor 108.

In an alternative (and with reference to FIG. 3), the at least one liquid sensor 108 can comprise a member emitting a signal 116 and a receiver member 117 of the signal, the receiver member operating in the housing chamber above and at a predetermined distance from the bottom. In this case it is not necessary for the liquid sensor to enter into contact with the liquid. For example, the emitter member can operate internally of the housing chamber above and at a predetermined distance from the bottom, such as to emit a signal crossing the collection zone (and thus any liquid accumulated in the collection zone) to be then reflected from the upper surface of the bottom towards the receiver member. The receiver member, according to the reflected signal received, can generate a measuring signal connected to the presence and/or the quantity of liquid present in the collection zone. It is specified that in an embodiment of the invention the emitter member can operate on the bottom, for example at the collection zone. Further, the emitter member and/or the receiver member can be constituted by a single member or a plurality of members adequately distributed on the transversal section of the housing chamber. As for typologies, the emitter member can comprise a member selected from a group comprising: an optical, acoustic, electric or electromagnetic signal emitter. Similarly, the receiver can comprise a member selected from a group comprising: a receiver of an optical, acoustic, electric or electromagnetic type.

The medical apparatus of any of the above-described embodiments can also comprise a user interface 118 and a programmed control unit 119 connected to the liquid sensor 108 and the user interface. The control unit 119 can for example comprise one or more digital microprocessor units or one or more analog units or other combinations of analog units and digital units. Relating by way of example to a microprocessor unit, once the unit has performed a special program (for example a program coming from outside or directly integrated on the microprocessor card), the unit is programmed, defining a plurality of functional blocks which constitute means each designed to perform respective operations. In an aspect of the invention, the programmed control unit defines:

means for receiving a measuring signal from the liquid sensor corresponding to detection of liquid presence and/or liquid level;

means for determining, depending on the measuring signal, the occurrence or not of an alarm condition;

means for commanding the user interface to generate a corresponding acoustic and/or visual signal, should an alarm condition be present.

In combination with one or more of the above characteristics, the medical apparatus can comprise at least one safety device operating at least the supply channel and commandable between at least one first operating condition, in which the safety device allows a liquid flow along the supply channel towards the treatment zone, and a second operative position, in which the safety device blocks passage of liquid towards the treatment zone. In this case, the control unit 119 can be connected to the safety device and programmed to define means for commanding the safety device to pass from the first to the second operative condition, should an alarm condition have been detected. In an embodiment, the safety device can for example comprise at least one check member connected to the control unit: the check member in the first operating condition and on command of the control unit closes the fluid passage from the source along the supply channel. In FIG. 1 the safety device is a solenoid valve 120 controlled by the unit 119 as described above. Obviously a valve of another nature, either an occlusive pump or a further member able to selectively prevent and enable fluid passage can be used.

Alternatively or additionally to the valve 120, the safety device can also comprise a bypass line 121 which connects the supply channel and the discharge channel, and one or more fluid check members 122 connected to the control unit for selectively opening and closing the bypass channel and the supply channel downstream of the bypass channel. The components 121 and 122, which can be alternative or additional to the presence of the member 120 are represented by a broken line in FIG. 1.

The check members 122 in the first operative condition and on command of the control unit close the fluid passage towards the treatment zone and connect the source with the discharge channel through the bypass line. Again with the aim of controlling the fluid passage towards the unit 4, pumps 2a and 6a can be included, located respectively on the lines 2 and 6 and also connected to the control unit 119.

Since the medical apparatus for blood treatment can comprise various liquid sources (for example one or more water sources 3, one or more concentrate sources 123, 124, one or more sources of disinfectant liquids 125) connected to the supply channel 2 with respective delivery lines 126, 127 and 128, the medical apparatus can exhibit, at each delivery line, a respective check member 129, 130, 131 (for example comprising a valve member and/or an occlusive pump).

In combination with one or more of the above-described characteristics, the medical apparatus can comprise means for electrical supply (such as one or more sources, electrical filters and the necessary electric power components of known type and therefore not described in detail herein) connectable to an electric supply source external to the apparatus and destined to distribute electrical energy coming from the outside at tensions, currents and frequencies which are correct for the medical apparatus. With reference to FIG. 1, the means for electric supply are schematically denoted by the block 132 and can be connected to the outside source, represented schematically by the block 140, with the interposing of means for selectively enabling and interrupting the electrical connection represented by the block 133. In a further embodiment, the programmed control unit 119 can be programmed to control means for selectively enabling and interrupting electrical energy 133 (such as for example a switch connected to the control unit) to the supply means on occurrence of the alarm condition.

Finally, again in combination with one or more of the above-described characteristics, the support structure of the medical apparatus can comprise: a predetermined number of internal walls 134 which separate the housing chamber into the various sub-compartments:

an upper chamber 135 located at the upper end of the housing chamber and housing the electronic circuitry 141, including the control unit 119, a first intermediate chamber 136 located at a vertically intermediate zone of the housing chamber, inferiorly with respect to the upper chamber 135, the first intermediate chamber housing the electrical source 132, a second intermediate chamber 137 located at a vertically intermediate zone of the housing chamber, inferiorly with respect to the upper chamber and adjacent to the first intermediate chamber, the second intermediate chamber housing one or more motors and one or more actuators, schematically denoted by the block 138 which can for example comprise the motors for the peristaltic pump or pumps 17 and the actuator for commanding the valve 16, a lower chamber 139, extending inferiorly of the intermediate chambers and above the bottom and housing the hydraulic circuit 1, the liquid sensor being housed in the lower chamber.

If the sensor is operating in the lower chamber the programmed control unit can include:

means for receiving a measuring signal from the liquid sensor corresponding to a detection of the presence of liquid and/or liquid level;

means for determining, depending on the measuring signal, the occurrence or not of an alarm condition, in which the means for determining the alarm condition verify the presence of an alarm condition before a liquid level in the bottom reaches the liquid sensor.

In other words the sensor is vertically distanced from the collection zone and the programmed control unit is programmed such that the alarm signal is generated before the liquid level reaches the sensor which is thus protected from immersion in the liquid.

As already mentioned, the described embodiments are intended to be non-limiting examples. In particular the circuits of FIG. 1 should not be interpreted as defining or limiting, as an apparatus such as in the invention can comprise other additional or alternative components to those described.

For example an ultrafiltration line can be included, with at least one respective pump connected to the discharge line. One or more infusion lines can also be included, with respective pumps or flow regulation valves, the infusion lines being connected up to the venous line 11 and/or the arterial line 9 and/or directly to the patient. The liquid sources can be pre-packaged bags and/or liquids prepared by the apparatus itself.

Finally, one or more pumps 2a, 6a and all the necessary temperature, pressure and concentration sensors can operate either on the supply line or on the discharge line, in order to adequately monitor the preparation and movement of the liquid in the hydraulic circuit.

The invention claimed is:

1. A medical apparatus for extracorporeal blood treatment, comprising:
    a support structure internally exhibiting a housing chamber, the housing chamber exhibiting at least one liquid collection zone,
    a hydraulic circuit having at least one supply channel, destined to transport a treatment liquid from at least one source towards a treatment station, and at least one discharge channel, destined to transport a used liquid from the treatment station towards an evacuation zone, the hydraulic circuit being located in the housing chamber above the liquid collection zone such that liquid leakage from the hydraulic circuit can at least partially accumulate in the liquid collection zone, a liquid sensor destined at least to detect presence of a liquid in the at least one liquid collection zone, wherein the liquid sensor operates in a distanced position with respect to the at least one liquid collection zone, and at least one measuring chamber and at least one enclosed channel which sets the at least one liquid collection zone in communication with the measuring chamber, the enclosed channel exhibiting a first end, connected to a lower point of the liquid collection zone, and a second end, connected to a wall of the measuring chamber, a longitudinal portion of the enclosed channel having a top surface, the top surface extending at a height which is vertically below at least a portion of a bottom of the liquid collection zone.

2. The medical apparatus of claim 1, wherein the support structure exhibits at least one lateral wall which substantially delimits the housing chamber and a bottom arranged at a lower portion of the support structure, the bottom comprising at least the liquid collection zone, the liquid sensor being located in a distanced position from the bottom.

3. The medical apparatus of claim 2, wherein the bottom exhibits a non-horizontal shape, the at least one liquid collection zone being arranged in a maximum-depth zone of the bottom in order to receive, by force of gravity, any liquid leakage coming from the hydraulic circuit.

4. The medical apparatus of claim 3, wherein the liquid sensor is located at a distanced position, which is vertically raised with respect to the liquid collection zone.

5. The medical apparatus of claim 4, wherein the bottom comprises a wall, which extends transversally of the lateral wall, substantially at a base zone of the support structure, the liquid sensor being located at a distanced position from the upper surface of the wall.

6. The medical apparatus of claim 5, wherein the bottom wall exhibits a perimeter edge, which is sealingly jointed to the lateral wall.

7. The medical apparatus of claim 5, wherein the bottom wall exhibits a perimeter edge developing in proximity of and adjacent to an internal surface of the lateral wall.

8. The medical apparatus of claim 1, wherein the liquid sensor comprises a liquid presence sensor operating in the measuring chamber, the sensor being located at a height which is vertically above the lowest point of the collection zone, the sensor emitting a measuring signal when the liquid level in the measuring chamber is greater than or equal to a level at which the presence sensor operates.

9. The medical apparatus of claim 1, wherein the liquid sensor comprises a liquid level sensor operating at the measuring chamber and emitting a measuring signal which is proportional to a liquid level in the measuring chamber.

10. The medical apparatus of claim 1, wherein the first end of the enclosed channel is directly connected to a lower point of the liquid collection zone, and the second end of the enclosed channel is directly connected to a lateral wall of the measuring chamber.

11. The medical apparatus of claim 1, wherein the measuring chamber comprises an upper opening for inspection, which develops substantially horizontally externally of a lateral wall of the support structure to enable direct access to the measuring chamber.

12. The medical apparatus of claim 1, wherein the liquid sensor comprises at least one emitter member of a signal and at least one receiver member of the signal, the receiver member operating in the housing chamber above and at a predetermined distance from a bottom arranged at a lower portion of the support structure.

13. The medical apparatus of claim 12, wherein the emitter member also operates internally of the housing chamber above and at a predetermined distance from the bottom, the emitter and the receiver being positioned and designed such that the emitter can emit a signal that crosses the collection zone and is reflected from the bottom towards the receiver member, the receiver member generating a measuring signal connected to a quantity of liquid present in the collection zone.

14. The medical apparatus of claim 13, wherein the emitter member comprises a member selected from a group comprising: an emitter producing an optical, an acoustic, an electrical or an electromagnetic signal.

15. The medical apparatus of claim 13, wherein the receiver member comprises a member selected from a group comprising: a receiver receiving an optical, an acoustic, an electrical or an electromagnetic signal.

16. The medical apparatus of claim 1, comprising at least one programmed control unit connected to the liquid sensor, the programmed control unit including at least:
   means for receiving a measuring signal from the liquid sensor corresponding to a detecting of presence of liquid and/or a liquid level;
   means for determining, depending on the measuring signal, the occurrence or not of an alarm condition.

17. The medical apparatus of claim 1, comprising: a user interface operatively associated with a front portion of the medical apparatus, a programmed control unit being connected to the user interface and including means for commanding the user interface to generate a corresponding acoustic and/or visible signal when a presence of an alarm condition is detected.

18. The medical apparatus of claim 16, comprising at least one safety device operating in at least the supply channel and commandable between at least one operating condition, in which the safety device enables a liquid flow along the supply channel towards the treatment station, and a second operating condition, in which the safety device prevents passage of liquid towards the treatment station, the control unit being connected to the safety device and programmed to define means for commanding the safety device to pass from the first operating condition to the second operating condition should an alarm condition be detected.

19. The medical apparatus of claim 18, wherein the safety device comprises at least one on-off member connected to the control unit, the on-off member, in the first operating condition and on command of the control unit, closing the fluid passage from the source along the supply channel.

20. The medical apparatus of claim 18, wherein the safety device comprises a bypass line which connects the supply channel and the discharge channel, and one or more fluid on-off members connected to the control unit, the fluid on-off member or members when in the first operating condition and on command of the control unit closing the fluid passage towards the treatment station and connecting the source with the discharge channel via the bypass line.

21. The medical apparatus of claim 18, wherein each source comprises a respective delivery line which sets a corresponding source in fluid communication with the supply channel, an on-off member comprising a valve member or an occlusive pump being included for each of the delivery lines.

22. The medical apparatus of claim 16, comprising:
electric supply means connected to an electric source external to the apparatus and destined to distribute electrical energy to the medical apparatus,
means for selectively enabling and interrupting electric supply to the supply means, the programmed control unit being programmed to control the means for selectively enabling and interrupting the electrical supply such as to disconnect the supply on detection of the alarm condition.

23. The medical apparatus of claim 1, wherein the support structure comprises:
a predetermined number of internal walls which separate the housing chamber into sub-compartments as follows:
an upper chamber extending at the upper end of the housing chamber and housing electrical circuitry, including a control unit,
a first intermediate chamber located at a vertically intermediate zone of the housing chamber, inferiorly with respect to the upper chamber, the first intermediate chamber housing means for electric supply,
a second intermediate chamber located at a vertically intermediate zone of the housing chamber, inferiorly with respect to the upper chamber and adjacent to the first intermediate chamber, the second intermediate chamber housing one or more motor members and one or more actuator members,
a lower chamber, extending inferiorly of the intermediate chambers and superiorly of a bottom and housing the hydraulic circuit.

24. The medical apparatus of claim 23, wherein the liquid sensor is housed in the lower chamber.

25. The medical apparatus of claim 24, comprising at least one programmed control unit connected to the liquid sensor, the programmed control unit comprising at least:
means for receiving a measuring signal from the liquid sensor which means correspond to a liquid presence detection and/or a liquid level detection;
means for determining, depending on the measuring signal, the occurrence or not of an alarm condition, the means for determining the alarm condition determining the existence of an alarm condition before a liquid level in the bottom reaches the liquid sensor.

26. A medical apparatus for extracorporeal blood treatment, comprising:
a support structure internally exhibiting a housing chamber, the housing chamber exhibiting a liquid collection zone,
a hydraulic circuit having at least one supply channel, destined to transport a treatment liquid from at least one source towards a treatment station, and at least one discharge channel, destined to transport a used liquid from the treatment station towards an evacuation zone, the hydraulic circuit being located in the housing chamber above the liquid collection zone such that liquid leakage from the hydraulic circuit can at least partially accumulate in the liquid collection zone,
a liquid sensor configured to detect presence of a liquid in the liquid collection zone, wherein the liquid sensor operates in a distanced position with respect to the liquid collection zone, and
a measuring chamber arranged externally of the housing chamber and an enclosed channel which sets the liquid collection zone in communication with the measuring chamber, a longitudinal portion of the enclosed channel having a top surface, the top surface extending at a height which is vertically below at least a portion of a bottom of the liquid collection zone, wherein the liquid sensor is arranged within the measuring chamber.

* * * * *

UNITED STATES PATENT AND TRADEMARK OFFICE
CERTIFICATE OF CORRECTION

PATENT NO. : 8,679,326 B2  
APPLICATION NO. : 12/809031  
DATED : March 25, 2014  
INVENTOR(S) : Vinci et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 455 days.

Signed and Sealed this

Twenty-ninth Day of September, 2015

Michelle K. Lee
*Director of the United States Patent and Trademark Office*